United States Patent
Ngo-Chu et al.

(10) Patent No.: US 10,857,333 B2
(45) Date of Patent: Dec. 8, 2020

(54) GUIDEWIRE WITH INTEGRAL EXPANDABLE DILATOR

(71) Applicant: Acclarent, Inc., Irvine, CA (US)

(72) Inventors: Don Q. Ngo-Chu, Irvine, CA (US); Jetmir Palushi, Irvine, CA (US); Itzhak Fang, Irvine, CA (US); Henry F. Salazar, Pico Rivera, CA (US); David A. Smith, Jr., Lake Forest, CA (US)

(73) Assignee: Acclarent, Inc., Irvine, CA (US)

( * ) Notice: Subject to any disclaimer, the term of this patent is extended or adjusted under 35 U.S.C. 154(b) by 277 days.

(21) Appl. No.: 15/822,509

(22) Filed: Nov. 27, 2017

(65) Prior Publication Data
US 2019/0160266 A1 May 30, 2019

(51) Int. Cl.
*A61M 25/09* (2006.01)
*A61B 5/06* (2006.01)
(Continued)

(52) U.S. Cl.
CPC ......... *A61M 25/09041* (2013.01); *A61B 1/07* (2013.01); *A61B 5/066* (2013.01);
(Continued)

(58) Field of Classification Search
CPC .......... A61M 25/0133; A61M 25/0136; A61M 25/0105; A61M 25/0138; A61M 25/0141; A61M 25/0144; A61M 25/0147; A61M 25/0155; A61M 25/09041; A61M 25/09025; A61M 25/09008; A61M 25/09;
(Continued)

(56) References Cited

U.S. PATENT DOCUMENTS

| 4,245,624 A | * | 1/1981 | Komiya | A61B 1/00098 600/106 |
| 4,723,936 A | * | 2/1988 | Buchbinder | A61M 25/0105 600/434 |

(Continued)

FOREIGN PATENT DOCUMENTS

| EP | 0563759 A1 | 10/1993 |
| WO | WO 89/04686 A1 | 6/1989 |

OTHER PUBLICATIONS

U.S. Appl. No. 62/555,824, entitled "Apparatus to Secure Field Generating Device to Chair," filed Sep. 8, 2017.

(Continued)

*Primary Examiner* — George J Ulsh
(74) *Attorney, Agent, or Firm* — Frost Brown Todd LLC

(57) ABSTRACT

A dilation apparatus includes a handle assembly, a dilator, a guidewire, and a steering assembly. The dilator is connected to the handle assembly and is configured to transition between an unexpanded state and an expanded state. The guidewire is longitudinally fixed relative to the dilator. The steering assembly is configured to laterally deflect at least a portion of the guidewire relative to the handle assembly. The steering assembly includes an actuator coupled with the handle assembly and a pull wire extending between the actuator and guidewire. A portion of the pull wire is attached to the guidewire. The actuator is configured to move the pull wire relative to the handle assembly in order to laterally deflect the at least a portion of the guidewire.

20 Claims, 14 Drawing Sheets

(51) Int. Cl.
A61B 17/24 (2006.01)
A61B 34/20 (2016.01)
A61B 1/07 (2006.01)
A61M 25/01 (2006.01)
A61M 29/02 (2006.01)
A61G 15/00 (2006.01)
A61B 17/00 (2006.01)
A61M 25/10 (2013.01)
A61B 90/30 (2016.01)
A61B 17/22 (2006.01)
A61B 1/00 (2006.01)
A61B 1/313 (2006.01)
A61M 3/02 (2006.01)

(52) U.S. Cl.
CPC ............ A61B 17/24 (2013.01); A61B 34/20 (2016.02); A61M 25/0147 (2013.01); A61M 25/09 (2013.01); A61M 29/02 (2013.01); A61B 1/00195 (2013.01); A61B 1/313 (2013.01); A61B 2017/003 (2013.01); A61B 2017/00323 (2013.01); A61B 2017/22051 (2013.01); A61B 2017/22062 (2013.01); A61B 2034/2051 (2016.02); A61B 2034/2072 (2016.02); A61B 2090/306 (2016.02); A61G 15/00 (2013.01); A61M 3/0283 (2013.01); A61M 2025/0166 (2013.01); A61M 2025/0186 (2013.01); A61M 2025/09008 (2013.01); A61M 2025/09083 (2013.01); A61M 2025/09175 (2013.01); A61M 2025/1093 (2013.01); A61M 2210/0681 (2013.01)

(58) Field of Classification Search
CPC ...... A61M 25/09016; A61M 25/09033; A61M 2025/015; A61B 2017/003; A61B 2017/00318; A61B 2017/00323; A61B 2017/00327; A61B 1/0052; A61B 1/0051; A61B 1/0053; A61B 1/0056; A61B 1/0057; A61B 1/008
See application file for complete search history.

(56) References Cited

U.S. PATENT DOCUMENTS

| | | | | |
|---|---|---|---|---|
| 4,787,399 A | | 11/1988 | Bonello et al. | |
| 4,976,689 A | * | 12/1990 | Buchbinder | A61M 25/09025 128/898 |
| 5,060,660 A | * | 10/1991 | Gambale | A61M 25/0144 600/585 |
| 5,125,895 A | * | 6/1992 | Buchbinder | A61M 25/09041 604/95.01 |
| 5,135,503 A | * | 8/1992 | Abrams | A61M 25/09 600/585 |
| 5,246,420 A | * | 9/1993 | Kraus | A61M 25/104 604/103.1 |
| 5,324,263 A | * | 6/1994 | Kraus | A61M 25/104 604/171 |
| 5,429,597 A | * | 7/1995 | DeMello | A61M 25/005 604/103.09 |
| 5,449,343 A | * | 9/1995 | Samson | A61M 25/0138 604/103.1 |
| 6,126,649 A | * | 10/2000 | VanTassel | A61M 25/0138 604/528 |
| 6,319,275 B1 | * | 11/2001 | Lashinski | A61F 2/958 606/108 |
| 7,720,521 B2 | | 5/2010 | Chang et al. | |
| 8,123,722 B2 | | 2/2012 | Chang et al. | |
| 8,190,389 B2 | | 5/2012 | Kim et al. | |
| 8,320,711 B2 | | 11/2012 | Altmann et al. | |
| 8,702,626 B1 | | 4/2014 | Kim et al. | |
| 9,167,961 B2 | | 10/2015 | Makower et al. | |
| 9,198,736 B2 | | 12/2015 | Kim et al. | |
| 2002/0066450 A1 | * | 6/2002 | Bonutti | A61M 16/0434 128/200.26 |
| 2002/0165571 A1 | * | 11/2002 | Hebert | A61B 17/12022 606/192 |
| 2004/0193205 A1 | * | 9/2004 | Burgermeister | A61M 25/0138 606/194 |
| 2005/0075661 A1 | * | 4/2005 | Levine | A61M 25/008 606/194 |
| 2007/0208252 A1 | | 9/2007 | Makower | |
| 2008/0172033 A1 | * | 7/2008 | Keith | A61B 1/00154 604/506 |
| 2008/0183128 A1 | | 7/2008 | Morriss et al. | |
| 2009/0318798 A1 | * | 12/2009 | Singh | A61B 1/012 600/424 |
| 2010/0030031 A1 | | 2/2010 | Goldfarb et al. | |
| 2010/0312101 A1 | * | 12/2010 | Drontle | A61M 25/0113 600/424 |
| 2011/0004057 A1 | | 1/2011 | Goldfarb et al. | |
| 2011/0060214 A1 | | 3/2011 | Makower | |
| 2011/0196410 A1 | * | 8/2011 | Besselink | A61F 2/013 606/191 |
| 2011/0264134 A1 | * | 10/2011 | Drontle | A61M 25/0113 606/199 |
| 2012/0078118 A1 | | 3/2012 | Jenkins et al. | |
| 2012/0203075 A1 | * | 8/2012 | Horvath | A61B 1/07 600/249 |
| 2012/0238819 A1 | * | 9/2012 | Long | A61B 1/00066 600/149 |
| 2014/0018732 A1 | | 1/2014 | Bagaoisan et al. | |
| 2014/0074141 A1 | | 3/2014 | Johnson et al. | |
| 2014/0200444 A1 | | 7/2014 | Kim et al. | |
| 2014/0243615 A1 | * | 8/2014 | Schaeffer | A61B 1/0057 600/301 |
| 2014/0275757 A1 | * | 9/2014 | Goodwin | A61F 2/2466 600/37 |
| 2014/0364725 A1 | | 12/2014 | Makower | |
| 2015/0202089 A1 | * | 7/2015 | Campbell | A61F 11/002 600/478 |
| 2016/0008083 A1 | | 1/2016 | Kesten et al. | |
| 2016/0310042 A1 | | 10/2016 | Kesten et al. | |
| 2017/0361064 A1 | * | 12/2017 | Golden | A61M 25/0043 |

OTHER PUBLICATIONS

International Search Report and Written Opinion dated Apr. 29, 2019 for International Application No. PCT/IB2018/059112, 19 pages.

* cited by examiner

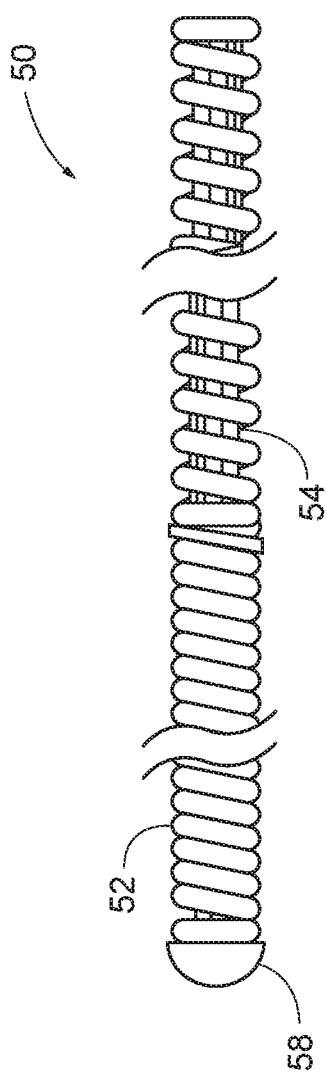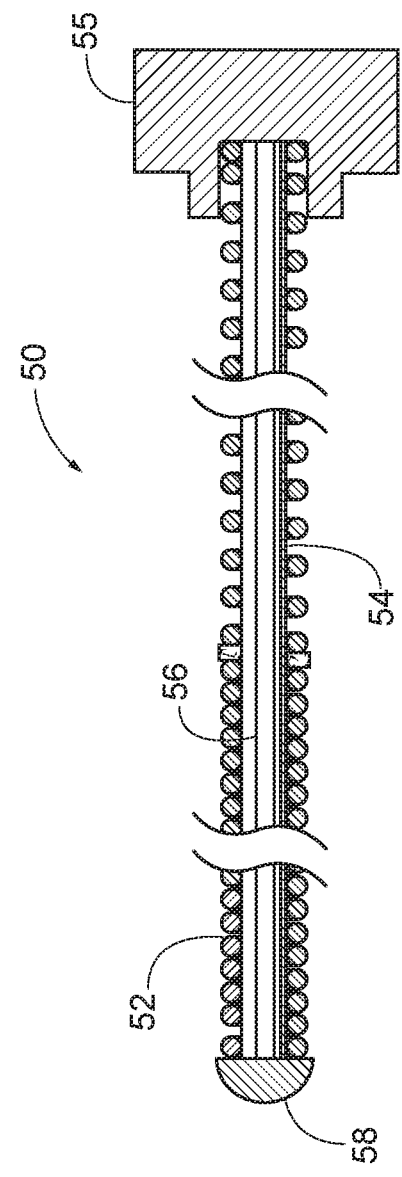

GUIDEWIRE WITH INTEGRAL EXPANDABLE DILATOR

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and guide catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Diamond Bar, Calif.; systems available from Surgical Navigation Technologies, Inc., of Louisville, Colo.; and systems available from Calypso Medical Technologies, Inc., of Seattle, Wash.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2-dimensional, line-of-sight view. The use of image guidance systems provides a real time, 3-dimensional view of all of the anatomy surrounding the operative field, not just that which is actually visible in the spatially limited, 2-dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

It may be desirable to provide easily controlled placement of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a detailed side elevational view of the illuminating guide wire of FIG. 2A;

FIG. 4 depicts a detailed side cross-sectional view of the illuminating guidewire of FIG. 2A;

Figure 1:
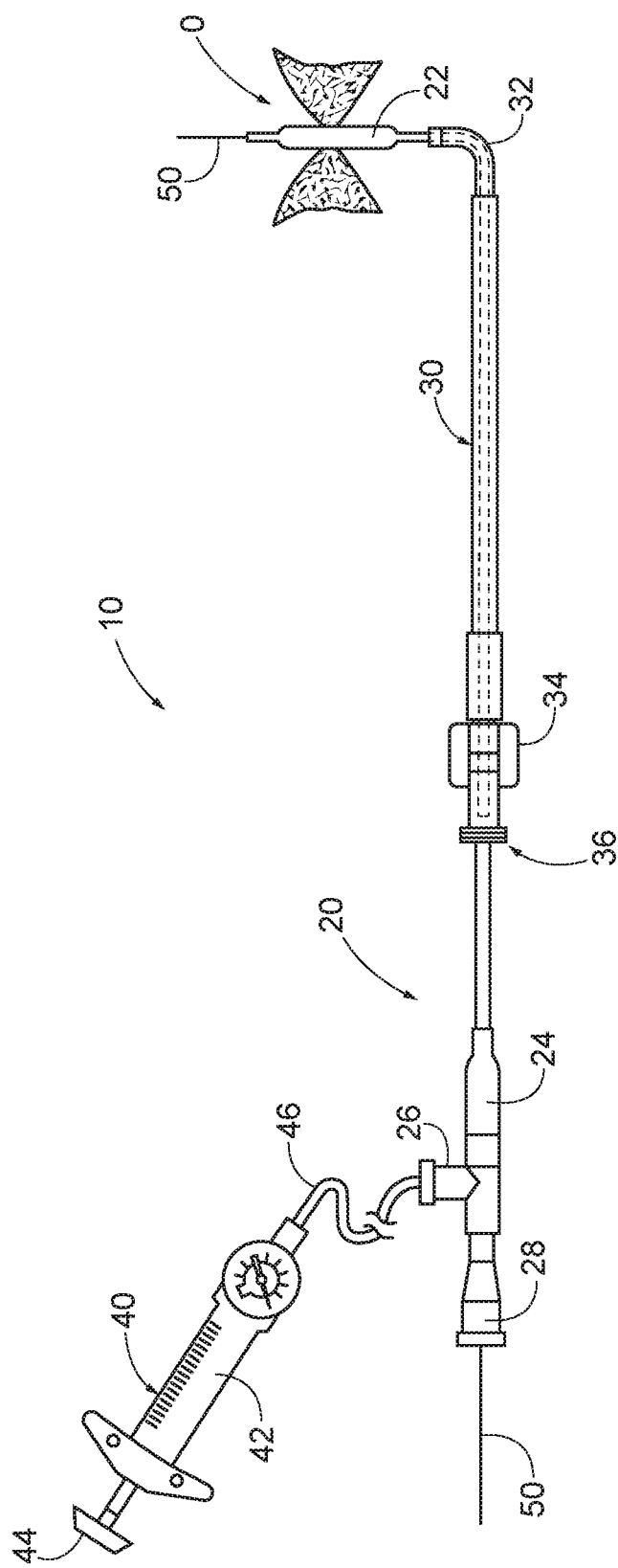
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Irvine, Calif.

Figure 2A:
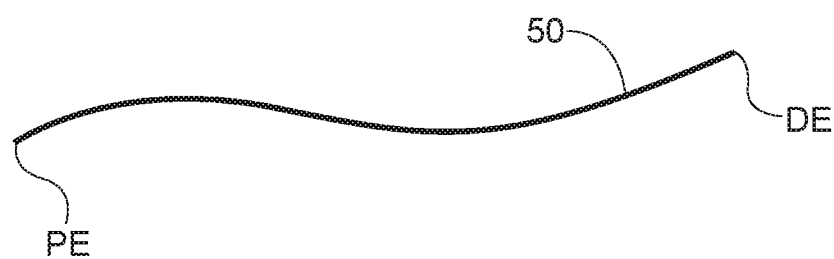
FIG. 2A depicts a side elevational view of an exemplary illuminating guidewire of the dilation catheter system of FIG. 1.
Figure 2B:
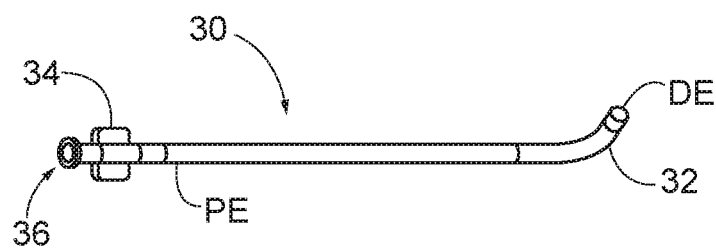
FIG. 2B depicts a side elevational view of an exemplary guide catheter of the dilation catheter system of FIG. 1.
Figure 2C:
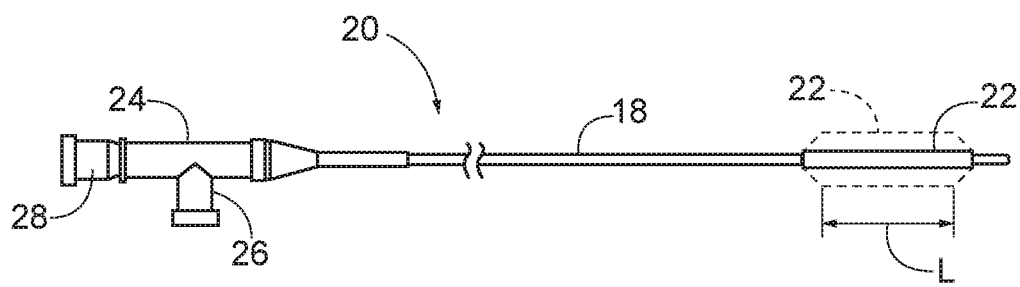
FIG. 2C depicts a side elevational view of an exemplary dilation catheter of the dilation catheter system of FIG. 1.

As best seen in FIG. 2C, the distal end (DE) of dilation catheter (20) includes an inflatable dilator (22). The proximal end (PE) of dilation catheter (20) includes a grip (24), which has a lateral port (26) and an open proximal end (28). A hollow-elongate shaft (18) extends distally from grip (24). Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Irvine, Calif. In some other versions, dilator catheter (20) is configured similar to the Relieva Solo Pro™ Sinus Balloon Catheter by Acclarent, Inc. of Irvine, Calif. Other suitable forms that dilator catheter (20) may take will be apparent to those of ordinary skill in the art in view of the teachings herein.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex™ Sinus Guide Catheter by Acclarent, Inc. of Irvine, Calif. Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, issued as U.S. Pat. No. 9,155,492 on Oct. 13, 2015, the disclosure of which is incorporated by reference herein. In some versions, guidewire (50) is configured similar to the Relieva Luma Sentry™ Sinus Illumination System by Acclarent, Inc. of Irvine, Calif. Other suitable forms that guidewire (50) may take will be apparent to those of ordinary skill in the art in view of the teachings herein.

II. Overview of Exemplary Endoscope

Figure 5:
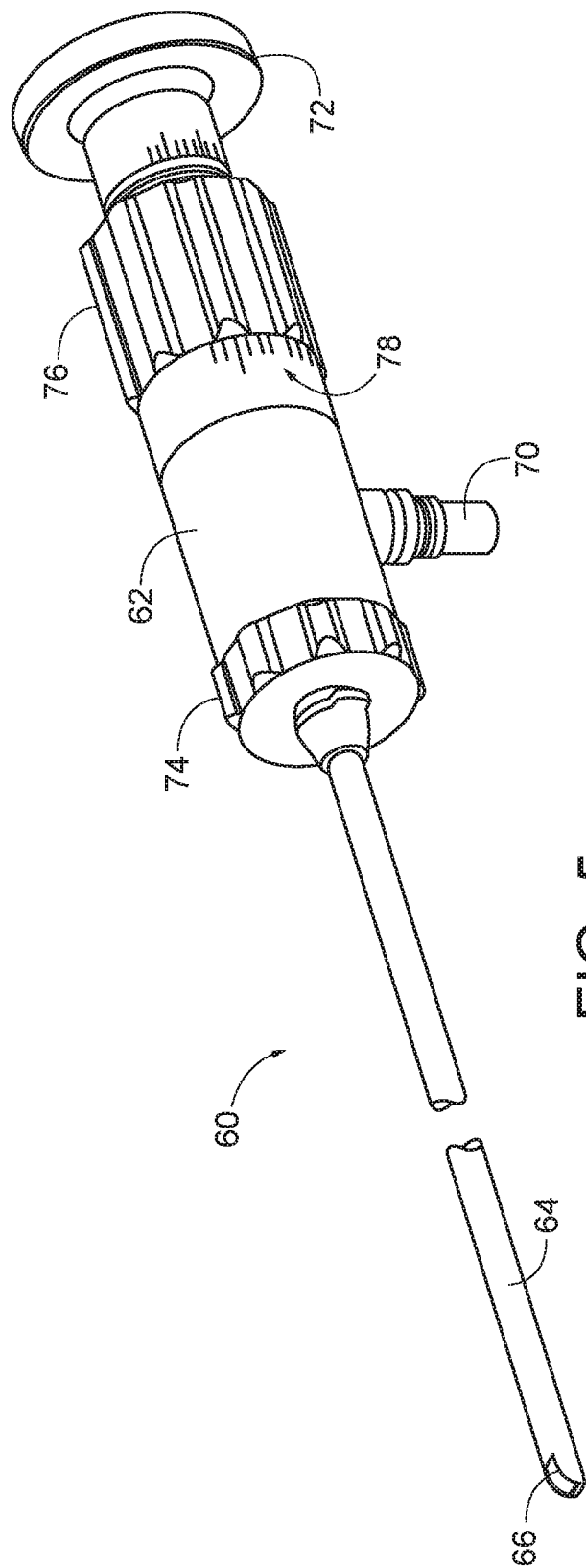
FIG. 5 depicts a perspective view of an exemplary endoscope suitable for use with the dilation catheter system of FIG. 1.

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. Other suitable forms that endoscope (60) may take will be apparent to those of ordinary skill in the art in view of the teachings herein III. Exemplary Method for Dilating the Ostium of a Maxillary Sinus FIGS. 7A-7E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 7A:
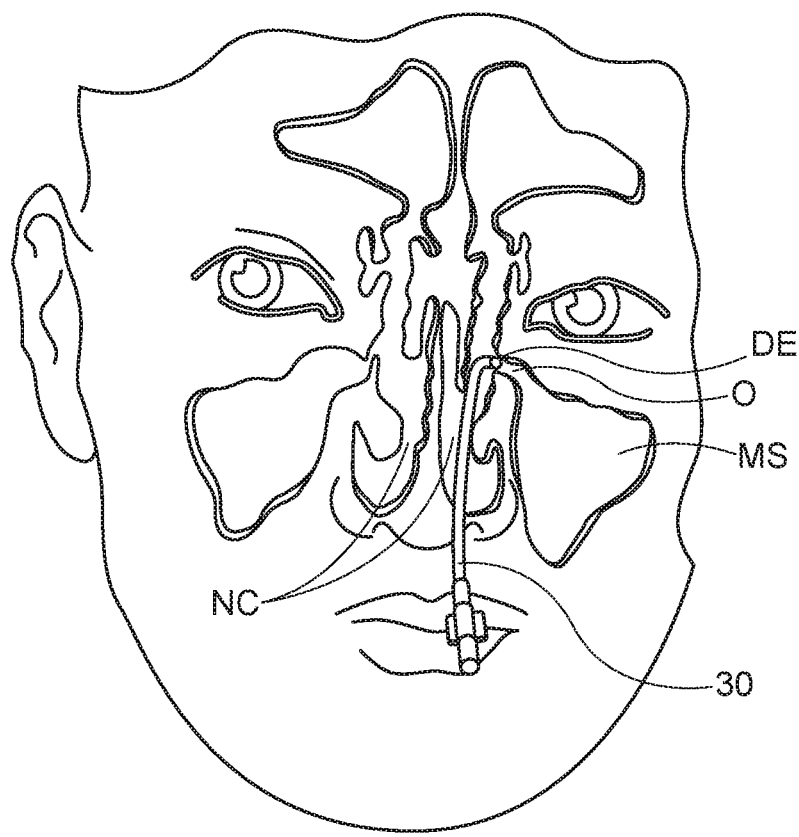
FIG. 7A depicts a front view of the guide catheter of FIG. 2B positioned adjacent an ostium of the maxillary sinus.
Figure 7C:
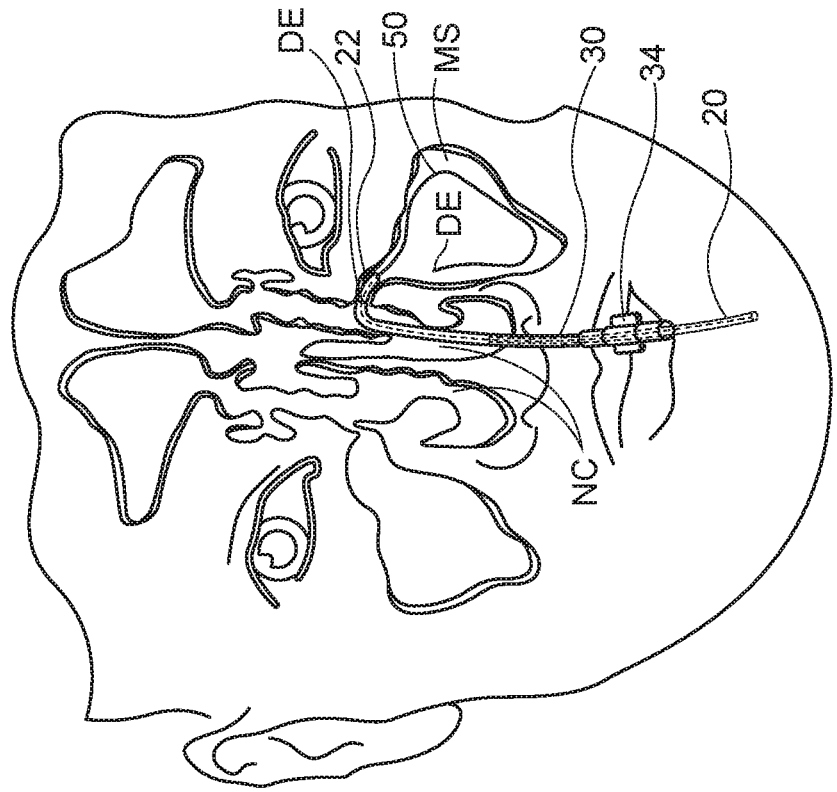
FIG. 7C depicts a front view of the guide catheter of FIG. 2B positioned adjacent an ostium of the maxillary sinus, with the illuminating guidewire of FIG. 2A translated further distally relative to the guide catheter and into the maxillary sinus.
Figure 7B:
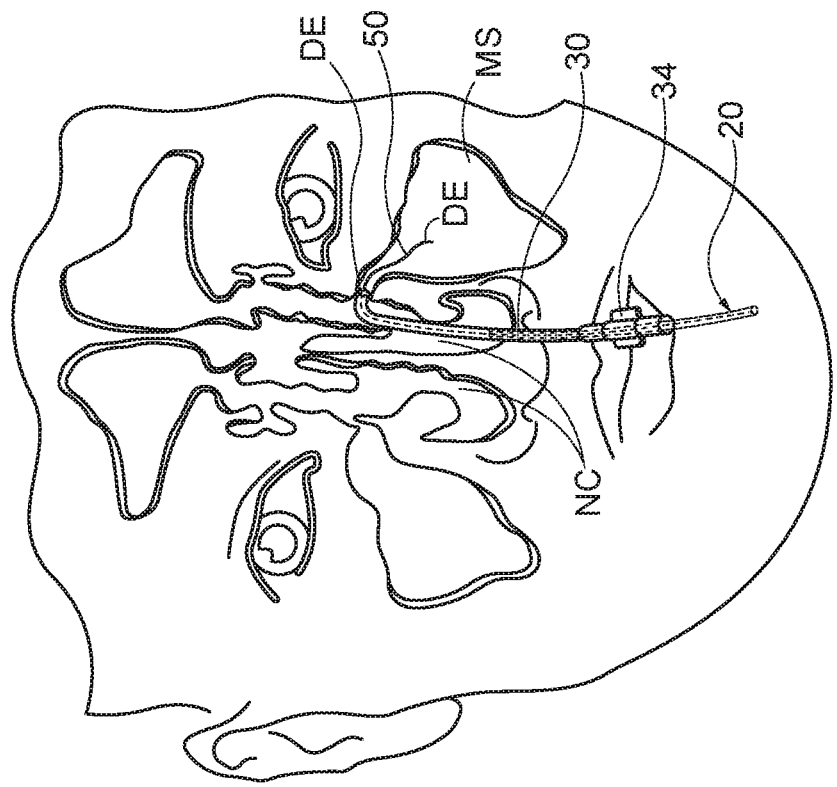
FIG. 7B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus.

In the procedure of the present example, guide catheter (30) may be inserted transnasally and advanced through the nasal cavity (NC) to a position within or near the targeted anatomical passageway to be dilated, the sinus ostium (O), as shown in FIG. 7A. Inflatable dilator (22) and the distal end of guidewire (50) may be positioned within or proximal to bent distal end (32) of guide catheter (30) at this stage. This positioning of guide catheter (30) may be verified endoscopically with an endoscope such as endoscope (60) described above and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 7B and 7C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 7E:
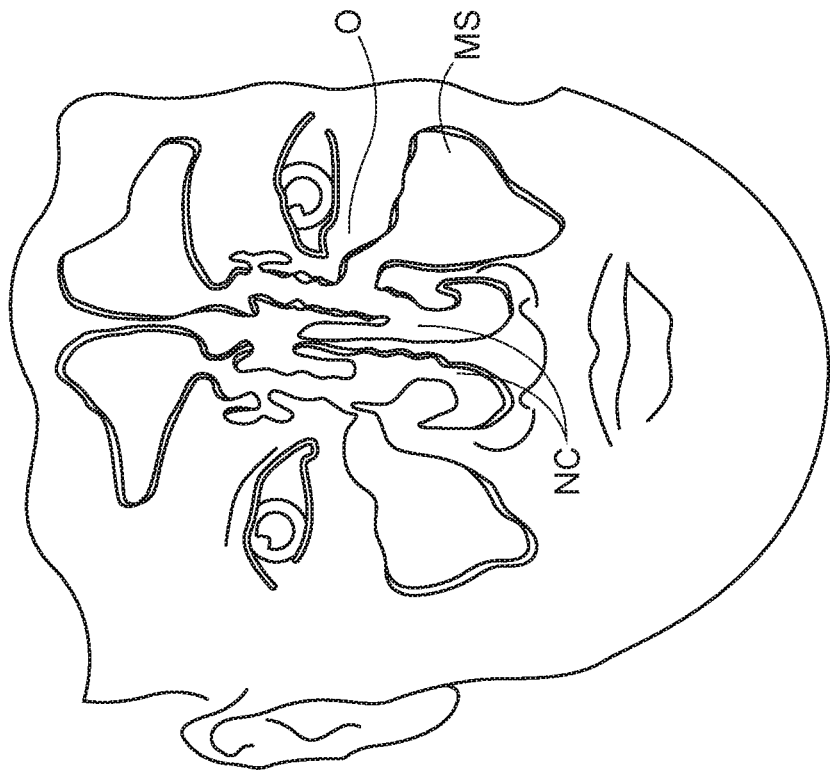
FIG. 7E depicts a front view of an ostium of the maxillary sinus, with the ostium having been enlarged by inflation of the balloon of FIG. 7D.
Figure 7D:
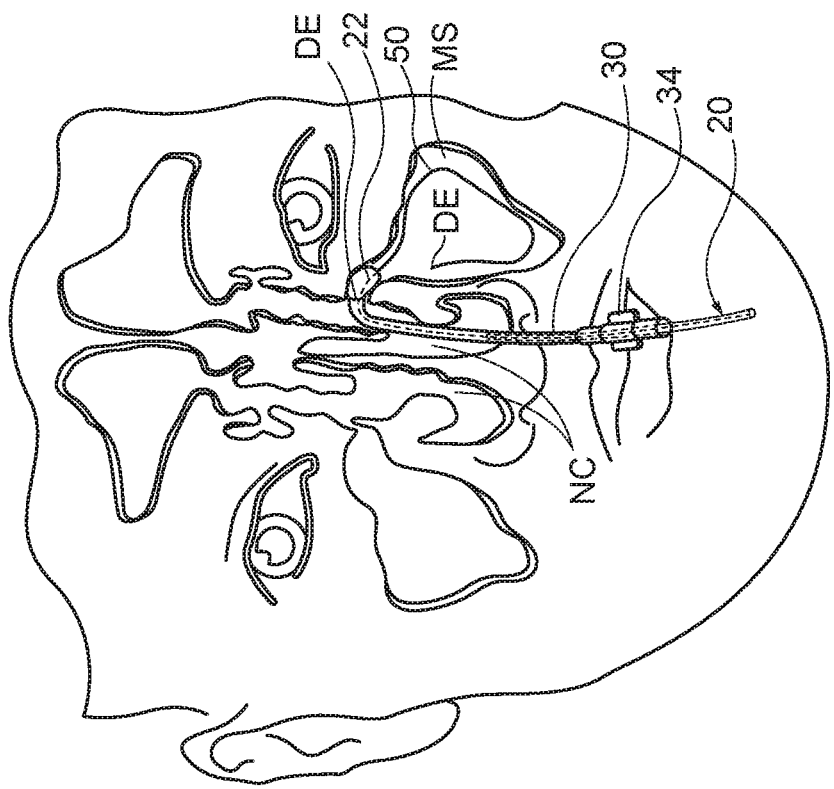
FIG. 7D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.

As shown in FIG. 7C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 7D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 7E.

In some instances, it may be desirable to irrigate the sinus and paranasal cavity after dilation catheter (20) has been used to dilate the ostium (0). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned. An example of an irrigation catheter that may be fed through guide catheter (30) to reach the irrigation site after removal of dilation catheter (20) is the Relieva Vortex® Sinus Irrigation Catheter by Acclarent, Inc. of Irvine, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Irvine, Calif. Of course, irrigation may be provided in the absence of a dilation procedure; and a dilation procedure may be completed without also including irrigation.

IV. Exemplary Image Guided Surgery Navigation System

Figure 8:
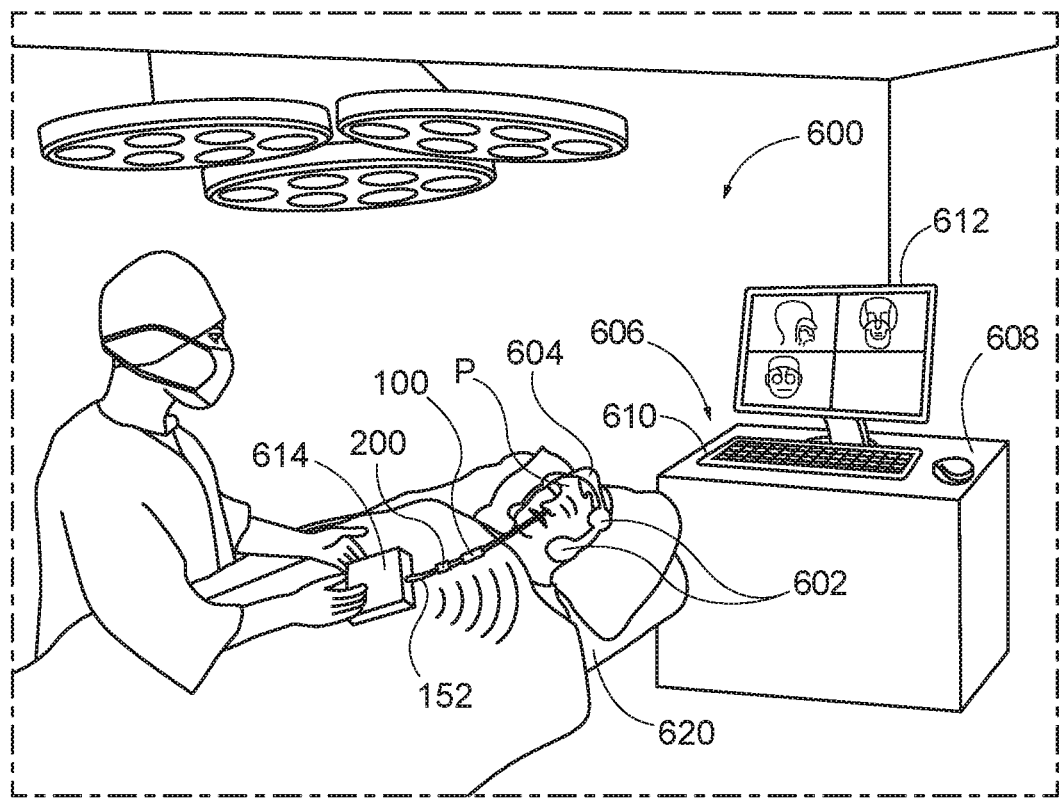
FIG. 8 depicts a schematic perspective view of an exemplary image-guided surgery navigation system.
Figure 9:
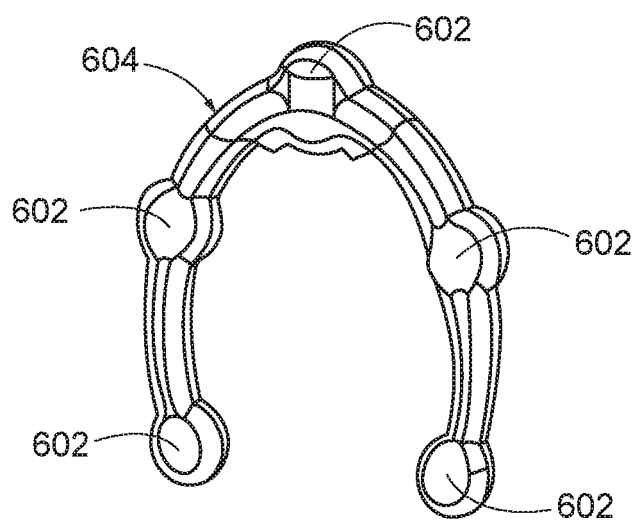
FIG. 9 depicts a perspective view of a frame component of the image-guided surgery navigation system of FIG. 8.

FIGS. 8 and 9 show an exemplary image-guided surgery (IGS) navigation system (600) configured to performed a Eustachian tube (ET) treatment procedure on a patient (P). As described in greater detail below, IGS navigation system (600) includes a computer used to obtain a real-time correlation of the location of an instrument that has been inserted into the patient's body, such as a balloon dilation catheter (200) that may be substantially similar to dilation catheter (20) described above, to a set of preoperatively obtained images (e.g., a CT or MRI scan, 3-D map, etc.) so as to superimpose the current location of the instrument on the preoperatively obtained images. In some instances, a digital tomographic scan (e.g., CT or MRI, 3-D map, etc.) of the operative field is obtained prior to surgery. A specially programmed computer is then used to convert the digital tomographic scan data into a digital map. During surgery, an instrument having one or more sensors (e.g., electromagnetic coils that emit electromagnetic fields and/or are responsive to externally generated electromagnetic fields) mounted thereon is used to perform the procedure while the sensors send data to the computer, indicating the current position of the surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real-time position of the surgical instrument relative to the anatomical structures shown in the scan images. In this manner, the surgeon is able to know the precise position of the sensor-equipped instrument by viewing the video monitor, even if the surgeon is unable to directly visualize the instrument itself at its current location within the body.

IGS navigation system (600) incorporates balloon dilation catheter (200) described above, and may further incorporate a suitable guide catheter (100) that may be substantially similar to guide catheter (30) described above. As described in greater detail below, IGS navigation system (600) is configured to implement a navigation sensor (not shown) at the distal end of dilation catheter (200) to provide real-time location tracking of the distal end of dilation catheter (200) within the patient (P) during a surgical procedure, and thereby facilitate accurate positioning of dilation catheter (200) within the patient (P). While IGS navigation system (600) is described below in connection with the positioning of balloon dilation catheter (200) and variations thereof within the ostium (O) of the maxilary sinus (MS), it will be appreciated that IGS navigation system (600) may also be employed in procedures for accessing and treating various other anatomical passageways of a patient with dilation catheter (200) and the variations thereof.

IGS navigation system (600) of the present example includes a set of magnetic field generators (602). Before a surgical procedure begins, field generators (602) are positioned about the head of the patient (P). As best shown in FIG. 9, in the present example field generators (602) arranged integrally within a frame (604) having a horseshoe-like shape and configured to be positioned about the patient's head. In the example of FIG. 8, patient (P) is positioned on a medical procedure table (620), and frame (604) is positioned above table (620) and about the patient's head. Frame (604) may be mounted to any suitable support structure (not shown), which may be coupled directly to medical procedure table (620) or provided independently from table (620), such as a floor-mounted stand. In other examples, frame (604) may be secured directly to the head of patient (P). It should be understood that field generators (602) may be positioned at various other suitable locations relative to patient (P), and on various other suitable structures.

Figure 11:
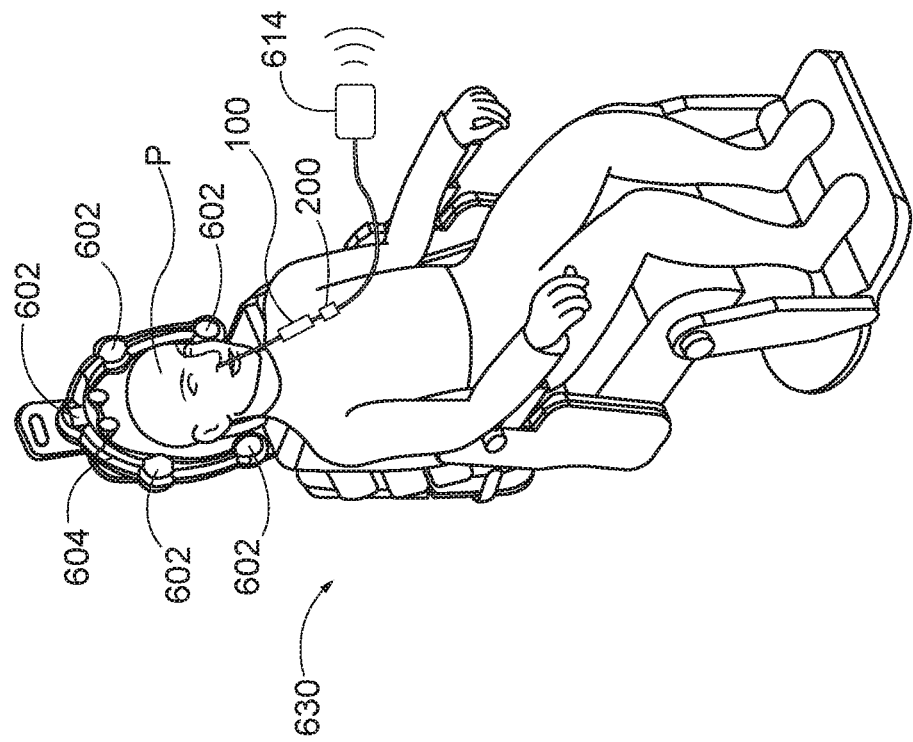
FIG. 11 depicts a perspective view of a patient seated in the medical procedure chair of FIG. 10, with the image-guided surgery navigation system of FIG. 8 being used to perform a procedure on the patient while seated in the chair.
Figure 10:
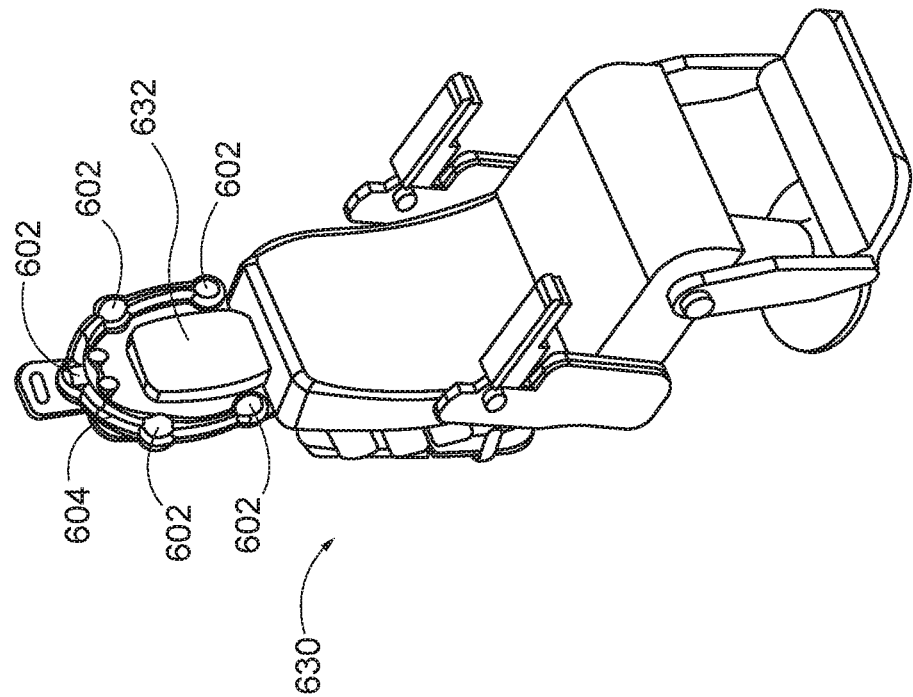
FIG. 10 depicts a perspective view of an exemplary medical procedure chair, with the frame component of the image-guided surgery navigation system of FIG. 9 mounted to the chair.

FIGS. 10 and 11 show another exemplary implementation of IGS navigation system (600), in which patient (P) is seated in a medical procedure chair (630). Frame (604) is mounted to a headrest (632) of chair (630) such that frame (604) extends about the head of patient (P) when seated in chair (630). Medical procedure chair (630) may be configured according to one or more teachings of U.S. Patent App. No. 62/555,824, entitled "Apparatus to Secure Field Generating Device to Chair," filed Sep. 8, 2017, the disclosure of which is incorporated by reference herein.

Field generators (602) of IGS navigation system (600) are operable to transmit alternating magnetic fields of different frequencies into a region in proximity to frame (604), and thereby generate an electromagnetic field in the region. In the present example, field generators (602) and frame (604) are arranged relative to the patient (P) such that the resulting electromagnetic field is formed about the patient's head. In other examples, field generators (602) and frame (604) may be suitably arranged in various other manners so as to generate an electromagnetic field about various other portions of the patient's body. Various suitable components that may be used to form and drive field generators (602) will be apparent to those of ordinary skill in the art in view of the teachings herein.

Field generators (602) enable tracking of the position of navigation sensor (not shown), and thus the distal end of balloon dilation catheter (200) when navigation sensor (not shown) moves through the electromagnetic field generated by field generators (602). In particular, as described in greater detail below, electromagnetic navigation sensor (not shown) of balloon dilation catheter (200) is configured to interact with the electromagnetic field and generate an electric signal in response to movement of sensor (not shown) through the electromagnetic field. Navigation sensor (not shown) then communicates this signal to a processor (606) of IGS navigation system (600). Processor (606), in turn, receives the signal and determines the three-dimensional location of navigation sensor (not shown), and the distal end of balloon dilation cathter (200) at which sensor (not shown) is arranged, within the electromagnetic field and thus the patient. While in the current example navigation sensor (not shown) is implemented at the distal end of dilation catheter (200), it should be understood that navigation sensor (not shown) may alternatively or additionally be implemented at the distal end of guidewire (50), the distal end of guide catheter (30, 100), or in any other suitable location within a suitable instrument as would be apparent to one having ordinary skill in the art in view of the teachings herein.

Processor (606) of IGS navigation system (600) comprises a processing unit that communicates with one or more memories, and is configured to control field generators (602) and other elements of IGS navigation system (600). In the present example, processor (606) is mounted in a console (608), which comprises operating controls (610) that include a keypad and/or a pointing device such as a mouse or trackball. A physician uses operating controls (610) to interact with processor (606) while performing the surgical procedure. Processor (606) uses software stored in a memory of processor (606) to calibrate and operate system (600). Such operation includes driving field generators (602), processing data received from navigation sensor (not shown), processing data from operating controls (610), and driving display screen (612). The software may be downloaded to processor (606) in electronic form, over a network, for example, or it may, alternatively or additionally, be provided and/or stored on non-transitory tangible media, such as magnetic, optical, or electronic memory.

Processor (606) is further operable to provide video in real time via display screen (612), showing the position of the distal end of balloon dilation catheter (200) in relation to a video camera image of the patient's head, a CT scan image of the patient's head, and/or a computer generated three-dimensional model of the anatomy within and adjacent to the patient's nasal cavity. Display screen (612) may display such images simultaneously and/or superimposed on each other. Moreover, display screen (612) may display such images during the surgical procedure. Such displayed images may also include graphical representations of instruments that are inserted in the patient's head, such as dilation catheter (200), such that the physician may view the virtual rendering of the instrument at its actual location in real time. Such graphical representations may look like the instrument or may be a much simpler representation such as a dot, crosshairs, etc. By way of example only, display screen (612) may provide images in accordance with at least some of the teachings of U.S. Pat. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the physician is simultaneously using an endoscope, such as endoscope (60) described above, the endoscopic image may also be provided on display screen (612). The images provided through display screen (612) may assist the physician in maneuvering and otherwise manipulating instruments within the patient's head.

Any suitable device may be used to generate a three-dimensional model of the internal anatomy of the portion of the patient's body (e.g., head) about which the electromagnetic field is generated and into which balloon dilation catheter (200) is to be inserted for conducting a treatment procedure. By way of example only, such a model may be generated in accordance with at least some of the teachings of U.S. Pat. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional anatomical model may be generated will be apparent to those of ordinary skill in the art in view of the teachings herein. It should also be understood that, regardless of how or where the three-dimensional model is generated, the model may be stored on console (608). Console (608) may thus render images of at least a portion of the model via display screen (612), and further render real-time video images of the position of the distal end of dilation catheter (200) in relation to the model via display screen (612).

Figure 6:
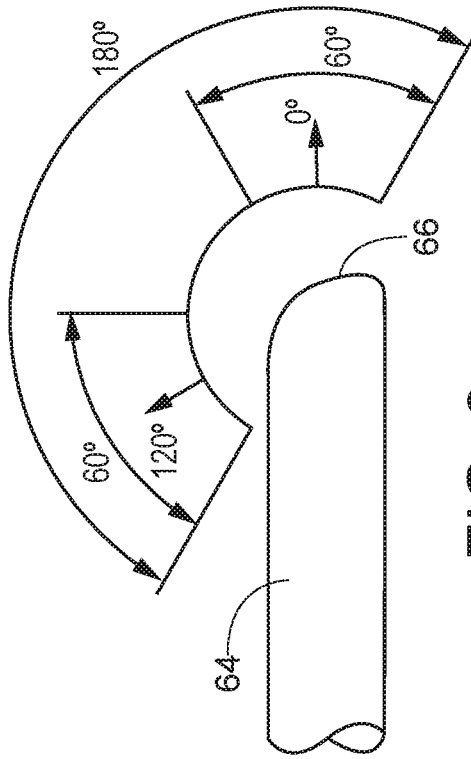
FIG. 6 depicts a side elevational view of the distal end of the endoscope of FIG. 5, showing an exemplary range of viewing angles.

In addition to connecting with processor (606) and operating controls (610), console (608) may also connect with other elements of IGS navigation system (600). For instance, as shown in FIG. 8, a communication unit (614) may be coupled with balloon dilation catheter (200) via wire (152), shown in FIG. 6. Communication unit (614) of this example is configured to provide wireless communication of data and other signals between console (608) and navigation sensor (not shown) of dilation catheter (200). In some versions, communication unit (614) simply communicates data or other signals from navigation sensor (not shown) to console (608) uni-directionally, without also communicating data or other signals from console (608). In some other versions, communication unit (614) provides bi-directional communication of data or other signals between navigation sensor (not shown) and console (608). While communication unit (614) of the present example couples with console (608) wirelessly, some other versions may provide wired coupling between communication unit (614) and console (608). Various other suitable features and functionality that may be incorporated into communication unit (614) will be apparent to those of ordinary skill in the art in view of the teachings herein.

In addition to, or in lieu of, having the components and operability described herein, IGS navigation system (600) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, IGS navigation system (600) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

V. Exemplary Devices Having Guidewires with Integral Expandable Dilators

In some instances, it may be desirable to combine various features of guidewire (50, 130) with various features of dilation catheter (20). Combining various features of dilation catheter (20) and guidewire (50, 130) into a single device may eliminate the need to actuate inflatable dilator (20) and guidewire (50, 130) separately relative to guide catheter (30) during exemplary use, thereby simplifying use. In addition to combining various features of dilation catheter (20) and guidewire (50, 130) into a single device, it may also be desirable to selectively steer (i.e. deflect) a distal end of the device during a procedure to assist an operator in locating and inserting the distal end of the device into the correct sinus passageway.

A. Exemplary Dilation Catheter with Integral Fixed Angled Guidewire

Figure 12:
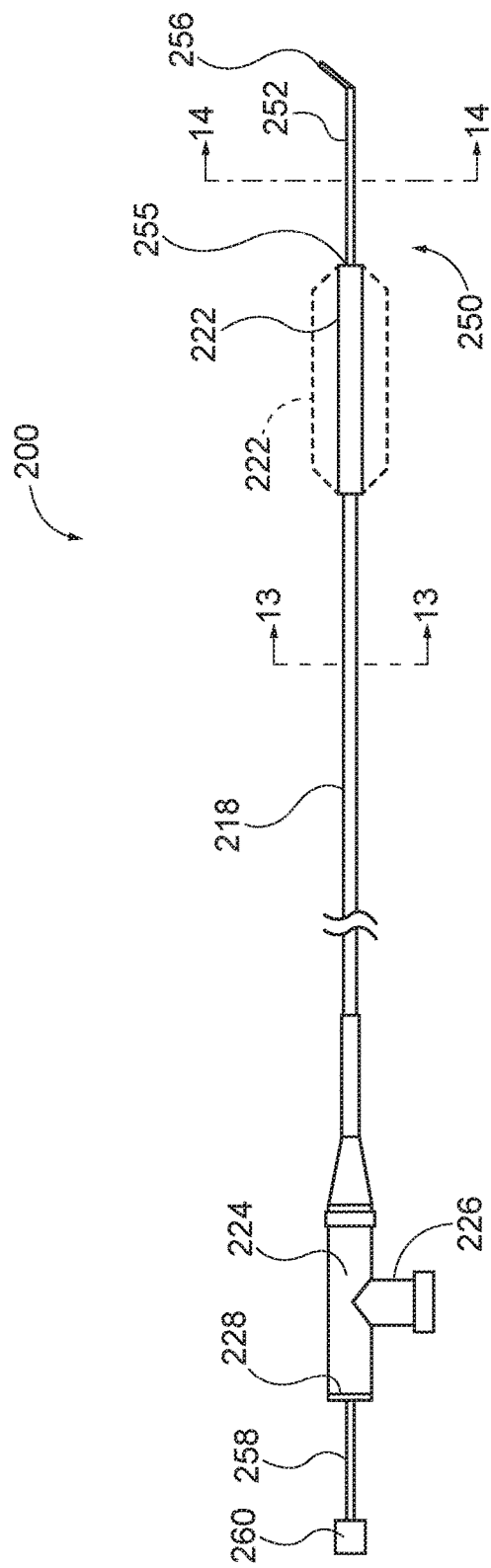
FIG. 12 depicts an elevational side view of an alternative dilation catheter.

FIGS. 10-12 show an exemplary alternative dilation catheter (202) that may be readily incorporated into either dilation catheter system (10) or IGS navigation system (600) described above. In particular, dilation catheter (202) may be incorporated into dilation catheter system (10) in replacement of both dilation catheter (20) and guidewire (50); while dilation catheter (202) may be incorporated into IGS navigation system (600) in replacement of dilation catheter (200).

As best seen in FIG. 12, dilation catheter (202) includes an inflatable dilator (222), a grip (224), a hollow-elongate shaft (218), and a distally extending fixed guidewire (250). Inflatable dilator (222), grip (224), and hollow-elongate shaft (218) may be substantially similar to inflatable dilator (22), grip (24) and hollow-elongate shaft (18) described above, respectively, with differences elaborated below. While in the current example an inflatable dilator (222) is used, any other suitable dilator may be used as would be apparent to one having ordinary skill in the art in view of the teachings herein. For example, a mechanical dilator may be used. As will be described in greater detail below, distally extending fixed guidewire (250) is fixedly attached to the rest of dilation catheter (200) via at least one fixed location (255) such that guidewire (250) may actuate with the rest of dilation catheter (200). In other words, guidewire (250) and dilation catheter (200) together form a unitary construction.

Grip (224) includes a lateral port (226) and an open proximal end (228). Shaft (218) defines a first lumen (230) and a second lumen (232) that are fluidly isolated from each other. Hollow-elongate shaft (218) extends distally from grip (224) into inflatable dilator (222). Hollow-elongate shaft (218) is resiliently flexible such that shaft (218) may deform if actuated through bent distal portion (32) of guide catheter (30), but also such that shaft (218) may retain its straight configuration when no longer constrained within bent distal portion (32).

First lumen (230) is in fluid communication with both lateral port (226) and the interior of inflatable dilator (222). Thus, lateral port (226) may fluidly couple with inflator (40) such that inflator (40) may add or withdraw fluid to/from dilator (222) via first lumen (230) in order to selectively inflate and deflate dilator (222). Second lumen (232) extends from open proximal end (228) of grip (224) all the way to an open distal end of inflatable dilator (222). However, unlike second lumen (now shown) of hollow elongated shaft (18), second lumen (232) does not slidably receive guidewire (250). Instead, distally extending fixed guidewire (250) is attached to the open distal end of inflatable dilator (222) at fixed location (255). Therefore, while distally extending fixed guidewire (250) may flex relative to inflatable dilator (222) and the rest of dilation catheter (200), guidewire (250) may not longitudinally translate relative to inflatable dilator (222). Therefore, an operator may actuate alternative dilation catheter (200) by pushing or pulling grip (224) in order to actuate both inflatable dilator (222) and guidewire (250).

Figure 14:
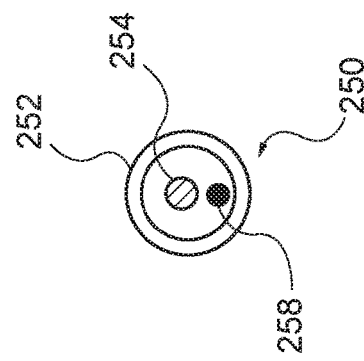
FIG. 14 depicts a cross-sectional view of the dilation catheter of FIG. 12, taken along line 14-14 of FIG. 12.
Figure 13:
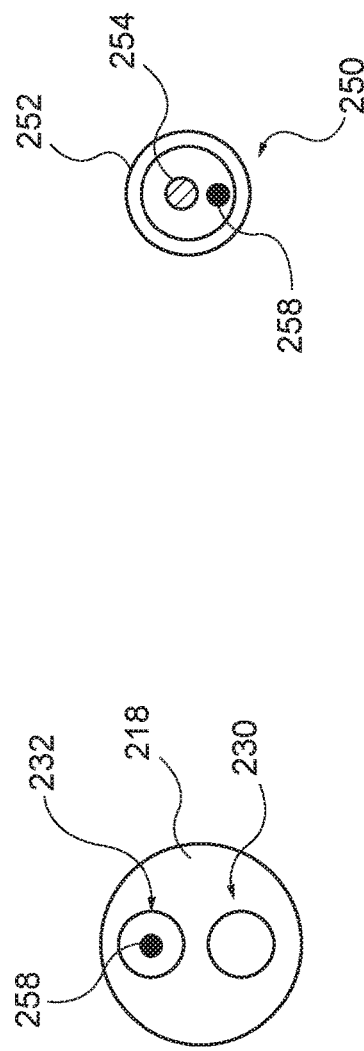
FIG. 13 depicts a cross-sectional view of the dilation catheter of FIG. 12, taken along line 13-13 of FIG. 12.

As best seen in FIGS. 12 and 14, distally extending fixed guidewire (250) includes a coil a (252) and a core wire (254), which are substantially similar to coil (52) and core wire (54) described above, with differences elaborated herein. Additionally, distally extending fixed guidewire (250) includes a bent distal end (256). Bent distal end (256) is resiliently biased toward a pre-set bent angle such that bent distal end (256) may deflect relative to the rest of guidewire (250). Therefore, bent distal end (256) may deflect from the pre-set bent angle when under an external force, and then may return to the pre-set bent angle when no longer under an external force. While in the current example, distally extending fixed guidewire (250) is attached to inflatable dilator (222) at a fixed location (255) that is distal to shaft (218), coil (252) and or core wire (254) may extend at least partially into second lumen (232), thereby placing fixed location (255) within shaft (218). Additionally, core wire (254) and coil (252) may be fixed at different longitudinal locations to either shaft (218) or inflatable dilator (222), thereby providing multiple fixed locations (255) in which guidewire (250) is attached to either inflatable dilator (222), hollow elongate shaft (218), or grip (224).

As best seen in FIGS. 10-12, dilation catheter (200) also includes an elongated connecting member (258). Elongated connecting member (258) extends from a coupling unit (260), through open proximal end (228) of grip (224), through second lumen (232), through inflatable dilator (222), and through the interior of guidewire (250) all the way to the tip of bent distal end (256). Coupling unit (260) may be directly attached to grip (224) such that coupling unit (260) and open proximal end (228) act as a second port. Elongated connecting member (258) and coupling unit (260) may be configured to adapt dilation catheter (200) for use with either dilation catheter system (10) or IGS navigation system (600).

For instance, if elongated connecting member (258) and coupling unit (260) are configured to adapt dilation catheter (200) with dilation catheter system (10), connecting member (258) and coupling unit (260) may be substantially similar to illumination fibers (56) and connector (55), respectively. Therefore, coupling unit (260) may be configured to couple with a light source while elongated connecting member (258) may be configured to communicate light from light source to the tip of bent distal end (256) for purposes of transillumination. Alternatively, elongated connecting member (258) and coupling unit (260) may be configured to adapt for use with IGS navigation system (600). Therefore, coupling unit (260) may be substantially similar to communication unit (614) described above. Additionally, elongated connecting member (258) may be substantially similar to wire (152) described above, such that connecting member (258) is connected to the tip of bent distal end (256), while the tip of bent distal end (256) acts as a navigation sensor similar to navigation sensor of dilation catheter (200). Therefore, when the sensing element of the tip of bent distal end (256) is positioned within an electromagnetic field generated by field generators (602), movement of the sensing element of bent distal end (256) within that magnetic field may generate electrical current within the tip of bent distal end (256), and this electrical current may be communicated along the electrical conduit(s) in elongated connecting member (258) and further to processor (606) via coupling unit (260). Of course, connecting member (258), coupling unit (260), as well as second lumen (232) are entirely optional.

B. Exemplary Guidewire Assembly with Integral Expandable Dilator

Figure 15:
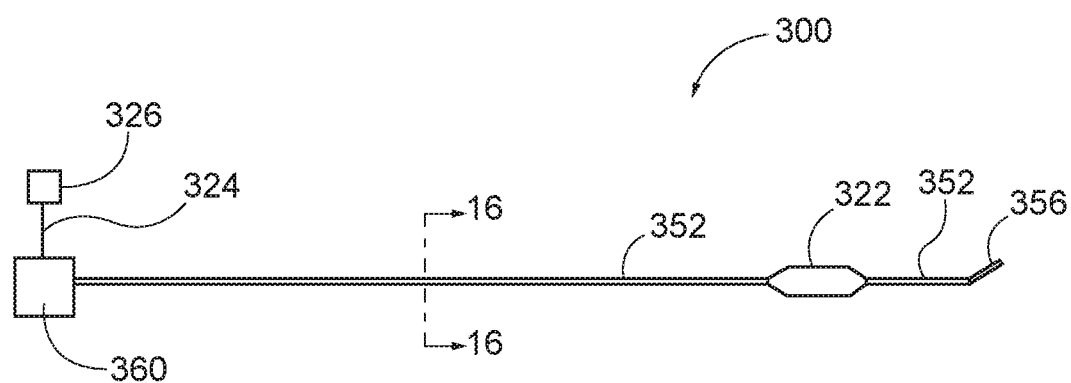
FIG. 15 depicts an elevational side view of an alternative guidewire having an integral expandable dilator.
Figure 16:
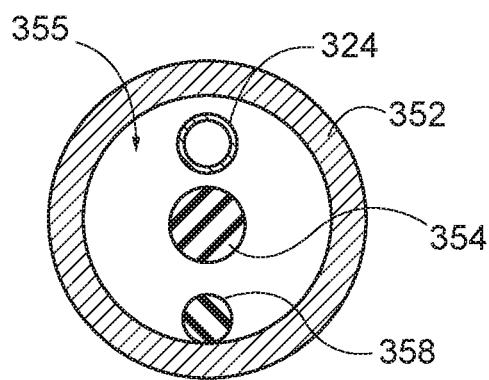
FIG. 16 depicts a cross-sectional view of the guidewire of FIG. 15, taken along line 16-16 of FIG. 15.
Figure 17:
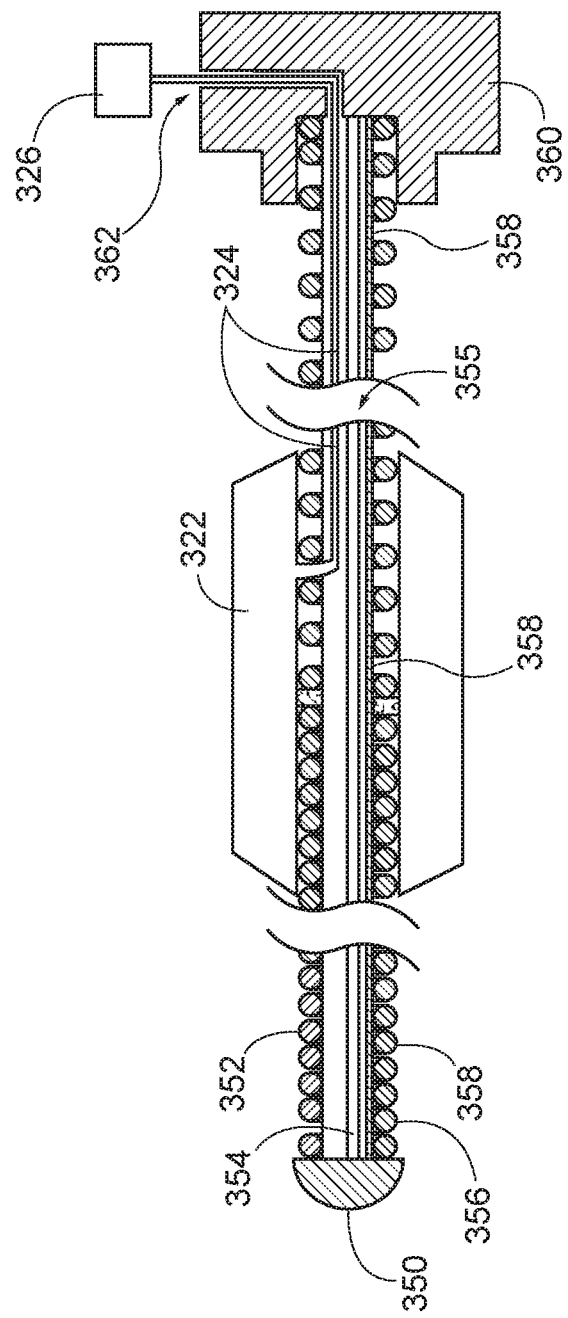
FIG. 17 depicts a detailed side cross-sectional view of the guidewire of FIG. 15.

FIGS. 15-17 show an exemplary guidewire assembly (300) that may be readily incorporated into either dilation catheter system (10) or IGS navigation system (600) described above. In particular, guidewire assembly (300) may be incorporated into dilation catheter system (10) in replacement of both dilation catheter (20) and guidewire (50); while guidewire assembly (300) may be incorporated into IGS navigation system (600) in replacement of dilation catheter (200).

Guidewire assembly (300) includes a coil (352), a core wire (354), and an elongated connecting member (358) extending from a coupling unit (360) and terminating at a bent distal end (356). Coil (352) and core wire (354) may be substantially similar to coil (52) and core wire (54) described above, respectively, with differences elaborated below. Coil (352) defines an interior (352) that houses core wire (354) and elongated connecting member (358). Bent distal end (356) is resiliently biased toward a pre-set bent angle such that bent distal end (356) may deflect relative to the rest of guidewire assembly (300). Therefore, bent distal end (356) may deflect from the pre-set bent angle when under an external force, and then may return to the pre-set bent angle when no longer under an external force.

Guidewire assembly (300) also includes an inflatable dilator (322) attached to an exterior portion of coil (352). Therefore, inflatable dilator (322) may actuate with the rest of guidewire assembly (300), such that dilator (322) is a unitary feature of guidewire assembly (300). As best seen in FIG. 17, an inflation tube (324) is in fluid communication with both inflatable dilator (322) and an inflation port (326). In particular, inflation tube (324) extends from inflation port (326), through a channel (362) defined by coupling unit (362), within interior (355) defined by coil (352), and through a gap defined by coil (352) to fluidly couple with inflatable dilator (322). In other words, inflation tube (324) extends from interior (355) of coil (352) to an exterior of coil (352) adjacent to inflatable dilator (322) in order to establish fluid communication with inflatable dilator (322). Inflation port (326) may fluidly couple with inflator (40) such that inflator (40) may add or withdraw fluid to/from dilator (222) via inflation tube (324) in order to selectively inflate and deflate dilator (322). Since inflatable dilator (322) is attached to coil (352), guidewire assembly (300) may serve as both a guidewire and a dilator.

Guidewire assembly (300) also includes an elongated connecting member (358). Elongated connecting member (358) extends from coupling unit (360), through interior (355) of guidewire (250) all the way to the tip (350) of bent distal end (356). Elongated connecting member (358) and coupling unit (360) may be configured to adapt guidewire assembly (300) for use with either dilation catheter system (10) or IGS navigation system (600).

For instance, if elongated connecting member (358) and coupling unit (360) are configured to adapt guidewire assembly (300) with dilation catheter system (10), connecting member (358) and coupling unit (360) may be substantially similar to illumination fibers (56) and connector (55), respectively. Therefore, coupling unit (360) may be configured to couple with a light source while elongated connecting member (358) may be configured to communicate light from light source to tip (350) of bent distal end (356) for purposes of trans illumination. Alternatively, elongated connecting member (358) and coupling unit (360) may be configured to adapt for use with IGS navigation system (600). Therefore, coupling unit (360) may be substantially similar to communication unit (614) described above. Additionally, elongated connecting member (358) may be substantially similar to wire (152) described above, such that connecting member (358) is connected to the tip of bent distal end (356), while the tip of bent distal end (356) acts as a navigation sensor similar to navigation sensor of dilation catheter (200). Therefore, when the sensing element of the tip of bent distal end (356) is positioned within an electromagnetic field generated by field generators (602), movement of the sensing element of bent distal end (356) within that magnetic field may generate electrical current in the one or more coils, and this electrical current may be communicated along the electrical conduit(s) in elongated connecting member (358) and further to processor (110) via coupling unit (360). Of course, connecting member (358) and coupling unit (360) are entirely optional.

C. Exemplary Alternative Dilation Catheter and Integral Guidewire Having Selective Steerability FIGS. 18A-20 show an exemplary alternative dilation catheter (400) that may be readily incorporated into either dilation catheter system (10) or IGS navigation system (600) described above. In particular, dilation catheter (400) may be incorporated into dilation catheter system (10) in replacement of both dilation catheter (20) and guidewire (50); while dilation catheter (400) may be incorporated into IGS navigation system (600) in replacement of dilation cathter (200).

Figure 18A:
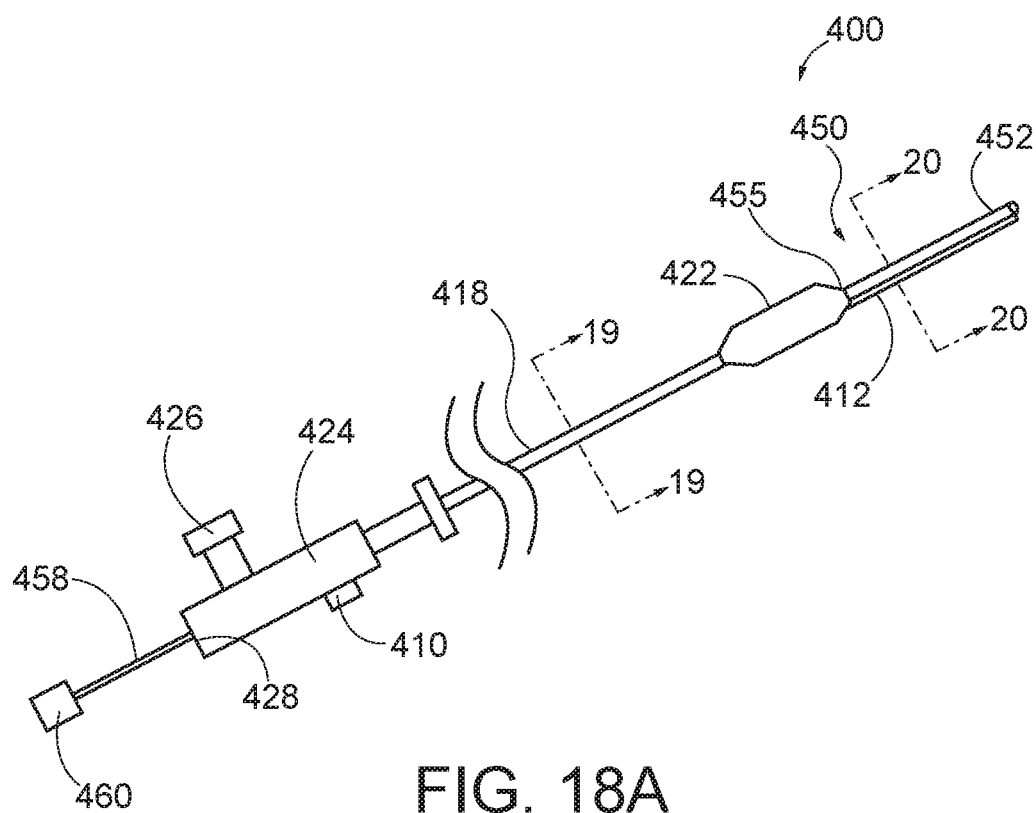
FIG. 18A depicts an elevational side view of an alternative dilation catheter, where a slider is in a first position and a distally extending fixed guidewire is in a straight configuration.
Figure 18B:
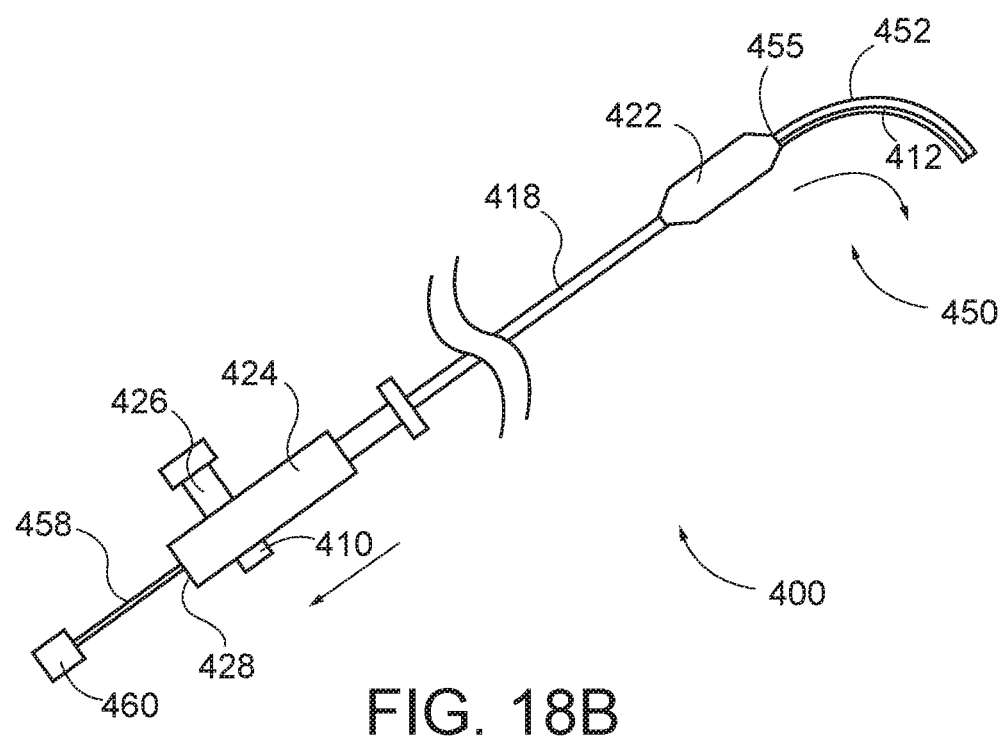
FIG. 18B depicts an elevational side view of the dilation catheter of FIG. 18A, where the slider is in a second position and the distally extending fixed guidewire is in a bent configuration.
Figure 19:
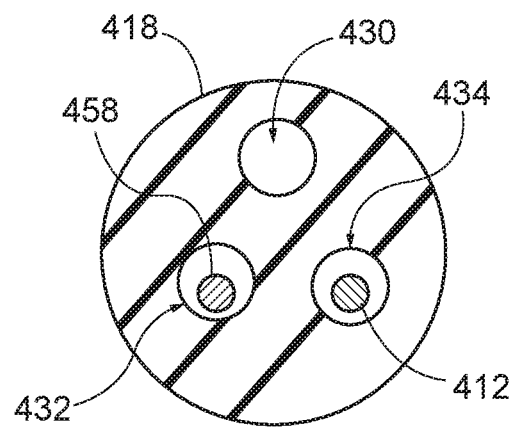
FIG. 19 depicts a cross-sectional view of the dilation catheter of FIG. 18A, taken along line 19-19 of FIG. 18A.
Figure 20:
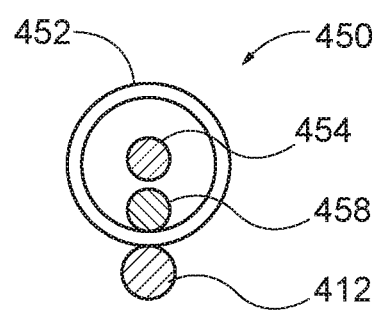
FIG. 20 depicts a cross-sectional view of the dilation catheter of FIG. 18A, taken along line 20-20 of FIG. 18A.

As best seen in FIGS. 18A-18B, dilation catheter (400) includes an inflatable dilator (422), a grip (424), a hollow-elongate shaft (418), and a distally extending fixed guidewire (450); which may be substantially similar to inflatable dilator (222), grip (224), hollow-elongate shaft (218), and distally extending fixed guidewire (250) described above, respectively, with differences described below. As will be described in greater detail below, dilation catheter (400) includes a slide (410) and a pull wire (412) configured to selectively steer (i.e. deflect) distally extending fixed guidewire (450) during a procedure.

Distally extending fixed guidewire (450) is fixedly attached to the rest of dilation catheter (400) via at least one fixed location (455) such that guidewire (450) may actuate with the rest of dilation catheter (400). In other words, guidewire (450) and dilation catheter (400) together form a unitary construction. While in the current example an inflatable dilator (222) is used, any other suitable dilator may be used as would be apparent to one having ordinary skill in the art in view of the teachings herein. For example, a mechanical dilator may be used.

Grip (424) includes a lateral port (426) and an open proximal end (428). Shaft (418) defines a first lumen (430), a second lumen (432), and a third lumen (434) that are fluidly isolated from each other. While in the current example, second lumen (432) And third lumen (434) are fluidly isolated from each other, this is merely optional. In fact, second lumen (432) and third lumen (434) may together form a single lumen, rather than two separate lumens. Hollow-elongate shaft (418) extends distally from grip (424) into inflatable dilator (422). Hollow-elongate shaft (418) is resiliently flexible such that shaft (418) may deform if actuated through bent distal portion (32) of guide catheter (30), but also such that shaft (418) may retain its straight configuration when no longer constrained within bent distal portion (32).

First lumen (430) is in fluid communication with both lateral port (426) and the interior of inflatable dilator (422). Thus, lateral port (426) may fluidly couple with inflator (40) such that inflator (40) may add or withdraw fluid to/from dilator (422) via first lumen (430) in order to selectively inflate and deflate dilator (422). Second lumen (232) extends from open proximal end (228) of grip (224) all the way to an open distal end of inflatable dilator (222). Distally extending fixed guidewire (450) is attached to the open distal end of inflatable dilator (422) at fixed location (455). Therefore, while distally extending fixed guidewire (450) may flex relative to inflatable dilator (422) and the rest of dilation catheter (400), guidewire (450) may not longitudinally translate relative to inflatable dilator (422). Therefore, an operator may actuate alternative dilation catheter (400) by pushing or pulling grip (424) in order to actuate both inflatable dilator (422) and guidewire (450).

Distally extending fixed guidewire (450) includes a coil a (452) and a core wire (454). While not shown, distally extending fixed guidewire (450) may also include a bent distal end substantially similar to bent distal end (256) decried above. While in the current example, distally extending fixed guidewire (450) is attached to inflatable dilator (422) at a fixed location (455) that is distal to shaft (418), coil (452) and or core wire (454) may extend at least partially into second lumen (432), thereby placing fixed location (245) within shaft (418). Additionally, core wire (454) and coil (452) may be fixed at different longitudinal locations to either shaft (418) or inflatable dilator (422), thereby providing multiple fixed locations (455) in which guidewire (450) is attached to either inflatable dilator (422), hollow elongate shaft (418), or grip (424).

Dilation catheter (400) also includes an elongated connecting member (458). Elongated connecting member (458) extends from a coupling unit (460), through open proximal end (428) of grip (424), through second lumen (432), through inflatable dilator (222), and through the interior of guidewire (450) all the way to the distal end of guidewire (450). Coupling unit (460) may be directly attached to grip (424) such that coupling unit (460) and open proximal end (428) act as a second port. Elongated connecting member (458) and coupling unit (240) may be configured to adapt dilation catheter (400) for use with either dilation catheter system (10) or IGS navigation system (600).

For instance, if elongated connecting member (458) and coupling unit (460) are configured to adapt dilation catheter (400) with dilation catheter system (10), connecting member (458) and coupling unit (460) may be substantially similar to illumination fibers (56) and connector (55), respectively. Therefore, coupling unit (460) may be configured to couple with a light source while elongated connecting member (458) may be configured to communicate light from light source to the distal end of guidewire (450) for purposes of transillumination. Alternatively, elongated connecting member (458) and coupling unit (460) may be configured to adapt for use with IGS navigation system (600). Therefore, coupling unit (460) may be substantially similar to communication unit (614) described above. Additionally, elongated connecting member (458) may be substantially similar to wire (152) described above, such that connecting member (458) is connected to the tip of guidewire (450), while the tip of guidewire (400) acts as a navigation sensor similar to navigation sensor of dilation catheter (200). Therefore, when the sensing element of the tip of guidewire (450) is are positioned within an electromagnetic field generated by field generators (602), movement of the one or more coils within that magnetic field may generate electrical current within the tip of guidewire (450), and this electrical current may be communicated along the electrical conduit(s) in elongated connecting member (458) and further to processor (606) via coupling unit (460). Of course, connecting member (458), coupling unit (460), as well as second lumen (432) are entirely optional.

As mentioned above, it may be desirable to assist an operator in locating and inserting the distal end of the device into the correct sinus passageway during a procedure. As also mentioned above, and as will be described in greater detail below, dilation catheter (400) includes a slide (410) and a pull wire (412) configured to selectively steer (i.e. deflect) distally extending fixed guidewire (450) during a procedure.

Slide (410) is slidably coupled to grip (424) such that slide (410) may longitudinally actuate along the profile of grip (424). Slide (410) is coupled with pull wire (412) such that actuation of slide (410) relative to grip (424) actuates pull wire (412) relative to grip (424). Pull wire (412) is slidably housed within third lumen (434) of shaft (418). Additionally, pull wire (412) extends distally past shaft (418) along the exterior of coil (452). In the current example, a distal tip of pull wire (412) is fixed to a distal tip of guidewire (450). However, pull wire (412) may be fixed along any suitable portion of guidewire (450) as would be apparent to one having ordinary skill in the art in view of the teachings herein.

As best shown between FIGS. 18A-18B, an operator may actuate slide (410) proximally relative to grip (424) such that pull wire (412) slides proximally relative to grip (424) and within third lumen (434). Because the distal tip of pull wire (412) is fixed to the distal tip of guidewire (450), guidewire (450) deflects away from the longitudinal axis defined by shaft (418). It should be understood that since guidewire (450) is coupled to inflatable dilator (422), inflatable dilator (422) may also deflect away from the longitudinal axis defined by shaft (418). Therefore, an operator may utilize slide (410) and pull wire (412) in order to steer/deflect guidewire (450) into a desired position for inserting guidewire (450) into a targeted passageway.

Pull wire (412) is resiliently biased toward the straight configuration as shown in FIG. 18A. Therefore, if an operator desires to deflect guide wire (450) back toward the straight configuration as shown in FIG. 18A, an operator may distally actuate slide (410) relative to grip (424) such that pull wire (314) slides distally relative to grip (424) and within third lumen (434). The resilient nature of pull wire (412) may straighten pull wire (412) and guidewire (450).

Slide (410) may be able to selectively lock its own longitudinal position relative to grip (424) such that an operator may help maintain the deflection at which guidewire (450) is deviated from the longitudinal axis of shaft (418). Various types of locking mechanism will be apparent to one having ordinary skill in the art in view of the teachings herein. For instance, slide (410) may be resiliently biased into frictional engagement with grip (424), such that an operator would have to overcome the bias to reduce the frictional breaking force between slide (410) and grip (424) in order to actuate slide (424) relative to grip (424).

While in the current example, a slide (410) is used in order to actuate pull wire (314). Various types of actuating mechanisms will be apparent to one having ordinary skill in the art in view of the teachings herein. For instance, a thumb wheel may be pivotally coupled with grip (424), such that rotation of thumb wheel may actuate pull wire (412) relative to grip (424) and shaft (418).

While in the current example, slide (410) and pull wire (412) are incorporated into a dilation catheter (400), slide (410) and pull wire (412) may be incorporated into guide wire assembly (300) having inflatable dilator (322). In examples where guidewire (450) includes a bent distal end, pull wire (412) may be fixed at a proximal end of the bent distal end. Alternatively, pull wire (412) may also be fixed at the distal end of the bent distal end, or any lactation between the distal end and proximal end of the bend distal end.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation apparatus, the dilation apparatus comprising: (a) a handle assembly; (b) a dilator configured to transition between an unexpanded state and an expanded state, wherein the dilator is connected to the handle assembly; (c) a guidewire extending distally from the dilator, wherein the guidewire is longitudinally fixed relative to the dilator, wherein the guidewire comprises a distal end; and (d) a steering assembly configured to laterally deflect at least a portion of the guidewire relative to the handle assembly, wherein the steering assembly comprises: (i) an actuator coupled with the handle assembly, and (ii) a pull wire extending between the actuator and guidewire, wherein a portion of the pull wire is attached to the guidewire, wherein the actuator is configured to move the pull wire relative to the handle assembly in order to laterally deflect the at least a portion of the guidewire.

Example 2

The dilation apparatus of Example 1, wherein the dilator comprises an inflatable dilator.

Example 3

The dilation apparatus of Example 2, further comprising a hollow-elongate shaft extending from the handle assembly to the inflatable dilator.

Example 4

The dilation apparatus of Example 3, wherein the hollow-elongate shaft defines a pull wire lumen, wherein the pull wire lumen slidably houses a portion of the pull wire.

Example 5

The dilation apparatus of Example 4, wherein the hollow-elongate shaft defines a first lumen in fluid communication with the inflatable dilator in order to transition the inflatable dilator from the unexpanded state to the expanded state.

Example 6

The dilation apparatus of Example 5, wherein the hollow-elongate shaft defines a second lumen housing an elongated connecting member, wherein the elongated connecting member extends from the handle assembly to the distal end of the guide wire.

Example 7

The dilation apparatus of Example 6, wherein the elongated connecting member is attached to a coupling unit.

Example 8

The dilation apparatus of Example 7, wherein the elongated connecting member comprises an illumination fiber.

Example 9

The dilation apparatus of any one or more of Examples 7 through 8, wherein the elongated connecting member comprises a coil, wherein the coil and the coupling unit are configured for use with an IGS navigation system.

Example 10

The dilation apparatus of any one or more of Examples 1 through 9, wherein the actuator comprises a slide.

Example 11

The dilation apparatus of any one or more of Examples 1 through 10, wherein the guidewire further comprises a bent distal end.

Example 12

The dilation apparatus of any one or more of Examples 1 through 11, wherein the pull wire is fixed at the distal end of the guidewire.

Example 13

The dilation apparatus of any one or more of Examples 1 through 12, wherein the guidewire extends between the handle assembly and the dilator.

Example 14

The dilation apparatus of any one or more of Examples 1 through 13, wherein the guidewire comprises a coil and a core wire, wherein the core wire defines an interior, wherein the core wire extends within the interior of the coil.

Example 15

The dilation apparatus of Example 14, wherein the pull wire is located on an exterior of the coil.

Example 16

A dilation apparatus, the dilation apparatus comprising: (a) a handle assembly; (b) an elongated shaft assembly extending distally from the handle assembly; (c) a dilator coupled with the elongated shaft, wherein the dilator is configured to transition from an unexpanded state to an expanded state; and (d) a guidewire extending distally from the dilator, wherein the guidewire is longitudinally fixed relative to the dilator, wherein the guidewire comprises: (i) a proximal portion defining an axis, and (ii) a distal portion comprising a bent distal end, wherein the bent distal end defines an oblique angle with the axis.

Example 17

The dilation apparatus of Example 16, wherein the bent distal end of the guidewire is resiliently biased toward the oblique angle.

Example 18

The dilation apparatus of any one or more of Examples 16 through 17, wherein the guidewire is fixed to the dilator.

Example 19

A dilation apparatus, the dilation apparatus comprising: (a) a guidewire extending from a proximal end to a distal end, wherein the guidewire comprises: (i) a coil comprising an exterior surface, wherein the coil defines an interior, and (ii) a core wire extending within the interior of the coil; (b) a connector coupled with the proximal end of the guidewire; (c) an inflatable dilator configured to transition between an inflated state and a deflated state, wherein the inflatable dilator is longitudinally fixed to the exterior surface of the coil; and (d) an inflation tube, wherein the inflation tube extends within the interior of the coil, wherein a portion of the inflation tube extends from the interior of the coil toward the exterior surface of the coil encompassed by the inflatable dilator, wherein the inflation tube is in fluid communication with the inflatable dilator.

Example 20

The dilation apparatus of Example 19, wherein the inflation tube extends through the connector and terminates into an inflation port.

Example 21

A method of using a dilation apparatus, the dilation apparatus comprising: (a) a handle assembly; (b) a dilator configured to transition between an unexpanded state and an expanded state, wherein the dilator is connected to the handle assembly; (c) a guidewire extending distally from the dilator, wherein the guidewire is longitudinally fixed relative to the dilator, wherein the guidewire comprises a distal end; and (d) a steering assembly configured to laterally deflect at least a portion of the guidewire relative to the handle assembly, wherein the steering assembly comprises: (i) an actuator coupled with the handle assembly, and (ii) a pull wire extending between the actuator and guidewire, wherein a portion of the pull wire is attached to the guidewire, wherein the actuator is configured to move the pull wire relative to the handle assembly in order to laterally deflect the at least a portion of the guidewire; the method comprising: (a) grasping the handle assembly and inserting the distal end of the guidewire into a nasal cavity of a patient; (b) manipulating the steering assembly to laterally deflect the guidewire relative to the handle assembly such that the distal end of the guidewire is adjacent to a targeted passageway; and (c) interesting the guidewire and a portion of the dilator into the targeted passageway.

Example 22

The method of Example 21, wherein the method further comprises transitioning the dilator from the unexpanded state to the expanded state.

Example 23

The method of either one of Examples 20 through 21, wherein manipulating the steering assembly further comprises translating the actuator relative to the handle assembly.

Example 24

The method of either one of Examples 20 through 21, wherein manipulating the steering assembly further comprises rotating the actuator relative to the handle assembly.

Example 25

A method of using a dilation apparatus, the dilation apparatus comprising: (a) a handle assembly; (b) an elongated shaft assembly extending distally from the handle assembly; (c) a dilator coupled with the elongated shaft, wherein the dilator is configured to transition from an unexpanded state to an expanded state; and (d) a guidewire extending distally from the dilator, wherein the guidewire is longitudinally fixed relative to the dilator, wherein the guidewire comprises: (i) a proximal portion defining an axis, and (ii) a distal portion comprising a bent distal end, wherein the bent distal end defines an oblique angle with the axis; wherein the method comprises: (a) grasping the handle assembly and inserting the bent distal end of the guidewire into a nasal cavity of a patient; and (b) further inserting at least a portion of the dilator into the nasal cavity of the patient.

Example 26

The method of Example 25, further comprising transitioning the dilator from the unexpanded state to the expanded state.

Example 26

The method of any one or more of Examples 25 through 26, wherein inserting the bend distal end of the guidewire into the nasal cavity of the patient further comprises deflecting the bend distal end of the guidewire relative to the proximal portion of the guidewire.

Example 27

A method of using a dilation apparatus, the dilation apparatus comprising: (a) a guidewire extending from a proximal end to a distal end, wherein the guidewire comprises: (i) a coil comprising an exterior surface, wherein the coil defines an interior, and (ii) a core wire extending within the interior of the coil; (b) a connector coupled with the proximal end of the guidewire; (c) an inflatable dilator configured to transition between an inflated state and a deflated state, wherein the inflatable dilator is longitudinally fixed to the exterior surface of the coil; and (d) an inflation tube, wherein the inflation tube extends within the interior of the coil, wherein a portion of the inflation tube extends from the interior of the coil toward the exterior surface of the coil encompassed by the inflatable dilator, wherein the inflation tube is in fluid communication with the inflatable dilator; the method comprising: (a) inserting the distal end of the guidewire into a nasal cavity of a patient; (b) further inserting at least a portion of the dilator into the nasal cavity of the patient; (c) transitioning the inflatable dilator from the deflated state to the inflated state by transferring fluid to the inflatable dilator via the inflation tube.

Example 28

The method of Example 27, further comprising transitioning the inflatable dilator from the inflated state to the deflate state by transferring fluid from the inflatable dilator via the inflation tube.

Example 29

The method of Example 28, further comprising removing the guidewire and the inflatable dilator from the nasal cavity of the patient.

Example 30

The method of any one or more of Examples 27 through 29, wherein the dealation apparatus further comprises a connecting member extending within the interior of the coil.

VII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A dilation apparatus, the dilation apparatus comprising:
   (a) a handle assembly;
   (b) a balloon configured to transition between an unexpanded state and an expanded state, wherein the balloon is connected to the handle assembly;
   (c) a guidewire extending distally from the balloon, wherein the guidewire is longitudinally fixed relative to the balloon, wherein the guidewire comprises a distal end;
   (d) a steering assembly configured to laterally deflect at least a portion of the guidewire relative to the handle assembly, wherein the steering assembly comprises:
      (i) an actuator coupled with the handle assembly, and
      (ii) a pull wire extending between the actuator and guidewire, wherein a portion of the pull wire is attached to the guidewire, wherein the actuator is configured to move the pull wire relative to the handle assembly in order to laterally deflect the at least a portion of the guidewire; and
   (e) a hollow-elongate shaft extending from the handle assembly to the balloon,
   wherein the guidewire is directly coupled to the balloon at a fixed location that is distally spaced apart from the hollow-elongate shaft.

2. The dilation apparatus of claim 1, wherein the hollow-elongate shaft defines a pull wire lumen, wherein the pull wire lumen slidably houses a portion of the pull wire.

3. The dilation apparatus of claim 2, wherein the hollow-elongate shaft defines a first lumen in fluid communication with the balloon in order to transition the balloon from the unexpanded state to the expanded state.

4. The dilation apparatus of claim 3, wherein the hollow-elongate shaft defines a second lumen housing an elongated connecting member, wherein the elongated connecting member extends from the handle assembly to the distal end of the guide wire.

5. The dilation apparatus of claim 4, wherein the elongated connecting member is attached to a coupling unit.

6. The dilation apparatus of claim 5, wherein the elongated connecting member comprises an illumination fiber.

7. The dilation apparatus of claim 5, wherein the elongated connecting member comprises a coil, wherein the coil and the coupling unit are configured for use with an IGS navigation system.

8. The dilation apparatus of claim 1, wherein the actuator comprises a slide.

9. The dilation apparatus of claim 1, wherein the guidewire further comprises a bent distal end.

10. The dilation apparatus of claim 1, wherein the pull wire is fixed at the distal end of the guidewire.

11. The dilation apparatus of claim 1, wherein the guidewire extends between the handle assembly and the balloon.

12. The dilation apparatus of claim 1, wherein the guidewire comprises a coil and a core wire, wherein the coil defines an interior, wherein the core wire extends within the interior of the coil.

13. The dilation apparatus of claim 12, wherein the pull wire is located on an exterior of the coil.

14. The dilation apparatus of claim 1, wherein the pull wire is resiliently biased toward a straight configuration, wherein the pull wire is configured to be parallel to the guidewire when the pull wire is in the straight configuration.

15. The dilation apparatus of claim 1, wherein the balloon includes a proximal balloon end and a distal balloon end, wherein the guidewire comprises a proximal guidewire end and a distal guidewire end, wherein the fixed location is at an interface between the proximal guidewire end and the distal balloon end.

16. The dilation apparatus of claim 15, wherein the guidewire includes a coil extending from the proximal guidewire end toward the distal guidewire end.

17. The dilation apparatus of claim 16, wherein the balloon is expandable from the proximal balloon end to the distal balloon end.

18. The dilation apparatus of claim 1, wherein the balloon includes a proximal balloon end, wherein the guidewire comprises a proximal guidewire end, wherein the balloon is expandable from the proximal balloon end to the proximal guidewire end.

19. A dilation apparatus, the dilation apparatus comprising:
(a) a handle assembly;
(b) a dilator configured to transition between an unexpanded state and an expanded state, wherein the dilator is connected to the handle assembly, wherein the dilator includes a proximal dilator end and a distal dilator end;
(c) a guidewire extending distally from the dilator, wherein the guidewire comprises a proximal guidewire end and a distal guidewire end, wherein the guidewire is directly coupled to the dilator at an interface between the proximal guidewire end and the distal dilator end such that the guidewire is longitudinally fixed relative to the dilator; and
(d) a steering assembly configured to laterally deflect at least a portion of the guidewire relative to the handle assembly, wherein the steering assembly comprises:
(i) an actuator coupled with the handle assembly, and
(ii) a pull wire extending between the actuator and guidewire, wherein a portion of the pull wire is attached to the guidewire, wherein the actuator is configured to move the pull wire relative to the handle assembly in order to laterally deflect the at least a portion of the guidewire,
wherein the guidewire includes a coil extending from the proximal guidewire end toward the distal guidewire end,
wherein the dilator is expandable along a length extending from the proximal dilator end to the distal dilator end.

20. A dilation apparatus, the dilation apparatus comprising:
(a) a handle assembly;
(b) a dilator having a distal end and being configured to transition between an unexpanded state and an expanded state, wherein the dilator is connected to the handle assembly;
(c) a guidewire having a proximal end and extending distally from the dilator, wherein the proximal end of the guidewire is fixed against movement relative to the distal end of the dilator; and
(d) a steering assembly configured to laterally deflect at least a portion of the guidewire relative to the handle assembly, wherein the steering assembly comprises:
(i) an actuator coupled with the handle assembly, and
(ii) a pull wire extending between the actuator and guidewire, wherein a portion of the pull wire is attached to the guidewire, wherein the actuator is configured to move the pull wire relative to the handle assembly in order to laterally deflect the at least a portion of the guidewire,
wherein the guidewire includes a coil terminating at the proximal end of the guidewire,
wherein the dilator is expandable along a length of the dilator to the distal end of the dilator.

\* \* \* \* \*